United States Patent
Klein

(10) Patent No.: US 10,352,769 B2
(45) Date of Patent: Jul. 16, 2019

(54) SELF-CALIBRATING SPECTRAL MODELS

(71) Applicant: The Boeing Company, Chicago, IL (US)

(72) Inventor: Robert J Klein, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 169 days.

(21) Appl. No.: 15/476,601

(22) Filed: Mar. 31, 2017

(65) Prior Publication Data

US 2018/0283943 A1 Oct. 4, 2018

(51) Int. Cl.
*G01J 3/28* (2006.01)
*G01N 21/27* (2006.01)
*G01N 21/01* (2006.01)

(52) U.S. Cl.
CPC .............. *G01J 3/28* (2013.01); *G01N 21/274* (2013.01); *G01N 2021/0118* (2013.01)

(58) Field of Classification Search
CPC ........... G01J 3/0297; G01J 3/2823; G01J 3/42
See application file for complete search history.

(56) References Cited

U.S. PATENT DOCUMENTS

| | | | |
|---|---|---|---|
| 8,249,308 B2* | 8/2012 | Lussier | G01J 3/02 356/300 |
| 8,848,173 B2* | 9/2014 | Poteet | G01N 21/55 356/73 |
| 2017/0010155 A1* | 1/2017 | Ritter | G01J 3/0297 |

OTHER PUBLICATIONS

Shippert, P., "Introduction to Hyperspectral Image Analysis", last accessed Jul. 20, 2016. http://spacejournal.ohio.edu/pdf/shippert.pdf.

* cited by examiner

*Primary Examiner* — Elias Desta
(74) *Attorney, Agent, or Firm* — Womble Bond Dickinson (US) LLP

(57) ABSTRACT

A method of implementing a self-calibrating database of spectral data includes receiving remotely-sensed spectral data for a geographic location. The method also includes accessing spectral data for a composition of materials at the geographic location from a database of spectral data for compositions of materials at respective geographic locations. The method includes calibrating the spectral data to match the remotely-sensed spectral data and thereby produce calibrated spectral data for the composition. The method includes validating the calibrated spectral data for the composition. And in an instance in which the calibrated spectral data for the composition is validated, the method includes replacing the spectral data with the calibrated spectral data to produce an enhanced database of spectral data for use in identifying materials or compositions of materials therefrom; and in at least one instance, outputting identifiers of the materials in the composition of materials.

21 Claims, 4 Drawing Sheets

SELF-CALIBRATING SPECTRAL MODELS

CROSS-REFERENCE TO RELATED APPLICATION(S)

The present application is related to U.S. patent application Ser. No. 15/201,136, entitled: Method and Apparatus for Simulating Spectral Information of Geographic Areas, U.S. patent application Ser. No. 15/201,137, entitled: Method and Apparatus for Using a Regionally Specific Spectral Model to Identify the Spectral Bands for use for Isolating Remotely Sensed Materials of Interest, and U.S. patent application Ser. No. 15/201,141, now U.S. Pat. No. 9,977,962, entitled: Method and Apparatus for On-Board Selection of Bands of a Hyperspectral Sensor Based on Simulated Spectral Representation of the Region of Interest, all of which filed on Jul. 1, 2016. The contents of all of the aforementioned are incorporated herein by reference.

TECHNOLOGICAL FIELD

The present disclosure relates generally to collecting spectral information and, in particular, to a self-calibrating spectral model of spectral data.

BACKGROUND

Mobile remote sensing platforms are a rich source of geographical data. Such mobile platforms may include aerial collection platforms such as aircraft and satellites in low-earth orbits (LEO), medium earth orbits (MEO), or geosynchronous/geostationary orbits. Mobile platforms use one or more sensors to collect geographical data. These sensors have a wide variety of sensor characteristics, including bandwidth, wavelengths resolution, and sensing technique, depending upon the application and information desired.

With regard to sensing techniques, the mobile remote sensing platform sensor(s) may be passive (e.g. simply sense energy emitted from targets). With regard to wavelengths, sensors may operate in a variety of bandwidths including ultraviolet, visual and infrared (near-infrared (NIR), short wave infrared (SWIR) and long wave infrared (LWIR). Sensor resolution may be defined in terms of spatial resolution (e.g. the pixel size of an image representing the area of the imaged surface as determined by the sensors' instantaneous field of view also referred to as ground sample distance (GSD); spectral resolution (e.g. the number of wavelengths (bands) collected), temporal resolution (e.g. the time period between measurements) and radiometric resolution (e.g. the effective bit depth or dynamic range of the sensor).

In many cases, mobile remote sensing platforms are used to search for and find "target" geographical features in a particular area. For example, a mobile remote sensing platform may be used to determine the extent of damage caused by a recent forest fire. In such cases, the sensor characteristics are usually chosen to maximize discriminants between the "target" and the background. Because the characteristics of the target and the background are typically not known apriori, this can be problematic, particularly with mobile remote sensing platforms, especially those mobile platforms that cannot be remotely configured in real or near real time.

One potential solution to this problem is to use hyperspectral imagers. Like other sensors or sensor suites, hyperspectral imagers collect and process data from across the electromagnetic wave spectrum. But unlike other multispectral imagers (which measure radiation reflected from a surface at a few wide, separated wavelength bands) hyperspectral imagers measure reflected radiation at a series of narrow and (typically) contiguous wavelength bands. This permits the gathering of more detailed spectral information which can provide much more information about the surface than a multispectral sensor and can reduce the guesswork in choosing how to best spectrally configure the mobile remote sensing platform sensor to collect information of interest.

However, this solution can severely stress hyperspectral imaging processing requirements on the mobile remote sensing platform and/or bandwidth and latency requirements of the communication link between the mobile remote sensing platform and the base station. Furthermore, while hyperspectral sensing might ease the planning of which spectral bands to collect, they do not solve and may well worsen sensor resolution and update concerns.

Therefore it would be desirable to have a system and method that takes into account at least some of the issues discussed above, as well as other possible issues.

BRIEF SUMMARY

To address the requirements described above, the above cited and incorporated '136, '137 and '141 applications describe systems and methods of geographic information system (GIS)-based spectral simulation. Example implementations of the present disclosure are generally directed to a system, and corresponding method and computer-readable storage medium for implementing a self-calibrating model including spectral data for compositions of materials that adds to this GIS-based spectral simulation. Example implementations calibrate the mixing of materials in a geographic area based on remotely-sensed data from a spectrally-limited multispectral satellite sensor (e.g., Landsat 8). Corrections at visual, NIR, and/or SWIR wavelengths may be made to the mixing of material components, rather than to the signature, and missing materials may be added to improve the model.

In some example implementations, recalibration is made constant as imagery is produced and the model is compared, which allows remixing incorrectly-classified pixels (due usually to change). As the materials are remixed on calibration rather than the signature being adjusted, spectral reflectance of a given area may be estimated at any wavelength in the electromagnetic spectrum, rather than just at the data points that are usually sampled in multispectral remote sensing. Well-mixed pixels (and the corresponding materials/percentages) may be fed into a machine learning algorithm as part of a training set that incorrectly classified or un-classified pixel values can be inferred against to redo mixing of unknown land classifications.

The present disclosure thus includes, without limitation, the following example implementations. Some example implementations provide a method of implementing a self-calibrating database of spectral data, the method comprising receiving remotely-sensed spectral data for a geographic location; accessing spectral data for a composition of materials at the geographic location from a database of spectral data for compositions of materials at respective geographic locations, the spectral data for the composition being a mixture of spectral data for the materials in respective percentages in the composition; calibrating the spectral data to match the remotely-sensed spectral data and thereby produce calibrated spectral data for the composition in which the materials are in respective percentages at least one of which is different from the spectral data; validating the calibrated spectral data for the composition; and in an instance in which the calibrated spectral data for the composition is validated, replacing the spectral data with the calibrated spectral data in the database of spectral data to produce an enhanced database of spectral data for use in identifying materials or compositions of materials therefrom; and in at least one instance, outputting identifiers of the materials in the composition of materials.

In some example implementations of the method of any preceding or any subsequent example implementation, or any combination thereof, the remotely-sensed spectral data is remotely-sensed multi-spectral data, and wherein the spectral data for the composition is a set of materials and corresponding spectral signatures accessed from a database of material spectral signatures, the spectral data for the composition being a mixture of the corresponding spectral signatures for the materials in respective percentages in the composition.

In some example implementations of the method of any preceding or any subsequent example implementation, or any combination thereof, the receiving remotely-sensed spectral data, accessing spectral data from the database of spectral data, calibrating the spectral data, validating the calibrated spectral data, and replacing the spectral data with the calibrated spectral data are repeatedly performed for different remotely-sensed spectral data to further enhance the enhanced database of spectral data.

In some example implementations of the method of any preceding or any subsequent example implementation, or any combination thereof, in each instance in which the calibrated spectral data for the composition is validated, the method further comprises associating the remotely-sensed spectral data with the composition of materials in the respective percentages, the remotely-sensed spectral data being associated with the composition in a training set of a machine learning algorithm.

In some example implementations of the method of any preceding or any subsequent example implementation, or any combination thereof, in at least one instance in which the calibrating fails to match the spectral data to the remotely-sensed spectral data, or in which the validating fails to validate the calibrated spectral data, the method further comprises using the machine learning algorithm to identify another composition of materials in respective percentages based on the training set that includes previous calibration results; and producing spectral data for the other composition of materials in the respective percentages, wherein the spectral data for the other composition is calibrated to match the remotely-sensed spectral data and thereby produce calibrated spectral data for the other composition, the calibrated spectral data for the other composition is validated, and the spectral data for the composition is replaced with the spectral data for the other composition in the database of spectral data.

In some example implementations of the method of any preceding or any subsequent example implementation, or any combination thereof, using the machine learning algorithm includes using the machine learning algorithm to identify the other composition of materials further based on the database of spectral data for compositions of materials at respective geographic locations.

In some example implementations of the method of any preceding or any subsequent example implementation, or any combination thereof, producing the spectral data for the other composition includes accessing spectral data for the materials in the other composition from a library of spectral data; and mixing the spectral data for the materials in the other composition in the respective percentages to produce the spectral data for the other composition.

Some example implementations provide an apparatus for implementing a self-calibrating database of spectral data. The apparatus comprises a processor and a memory storing executable instructions that, in response to execution by the processor, cause the apparatus to at least perform the method of any preceding example implementation, or any combination thereof. This may include implementation of a system for implementing a self-calibrating database of spectral data including a calibration subsystem and validation subsystem coupled to one another and configured to perform steps of the method.

Some example implementations provide a computer readable medium for implementing a self-calibrating database of spectral data. The computer-readable storage medium is non-transitory and having computer-readable program code portions stored therein that, in response to execution by a processor, cause an apparatus to at least perform the method of any preceding example implementation, or any combination thereof.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described example implementations of the disclosure in general terms, reference will now be made to the accompanying drawings, which are not necessarily drawn to scale, and wherein:

DETAILED DESCRIPTION

Figure 1:
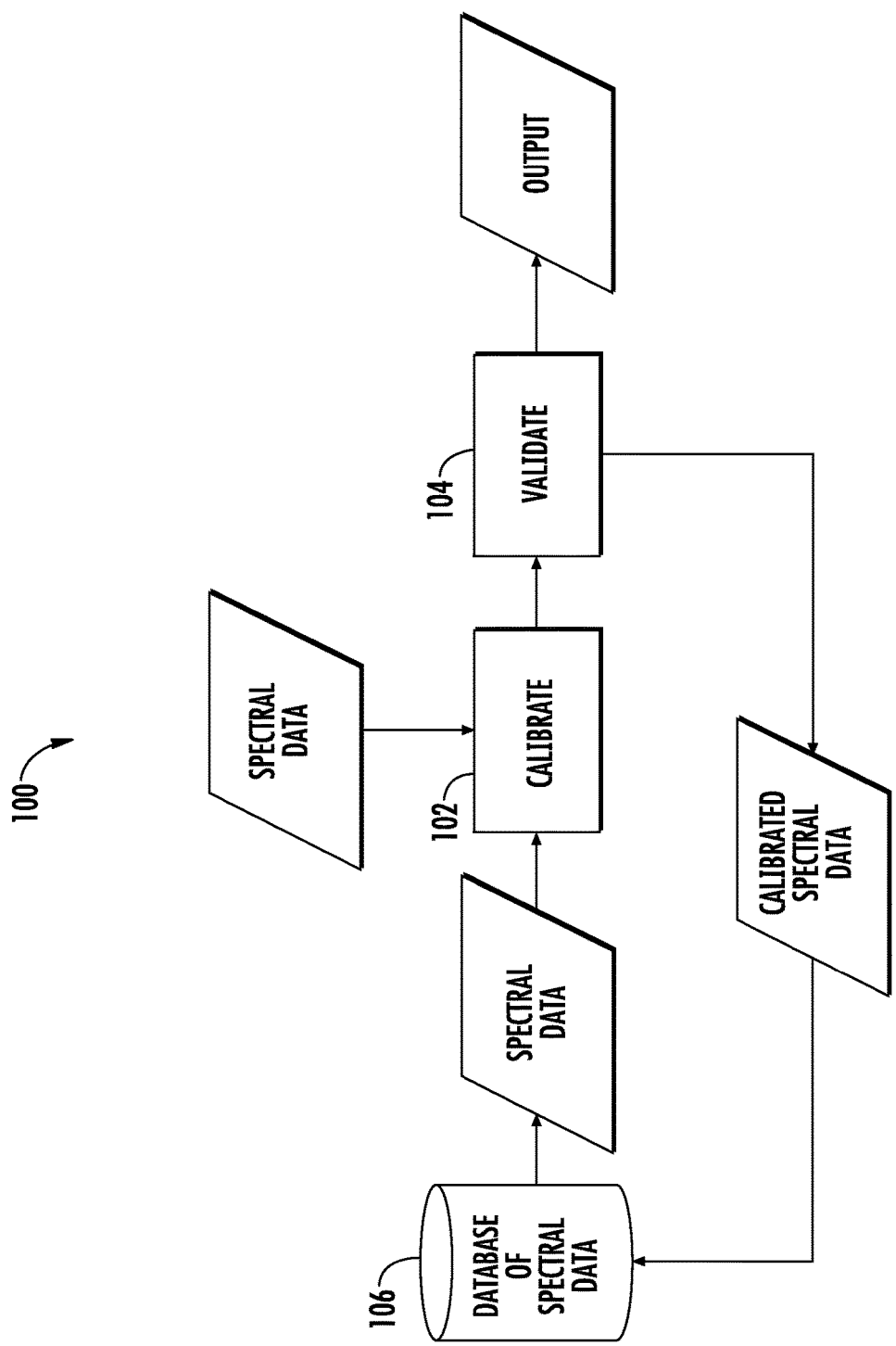
FIG. 1 illustrates a system according to example implementations of the present disclosure.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. For example, unless otherwise indicated, reference to something as being a first, second or the like should not be construed to imply a particular order. Also, for example, reference may be made herein to quantitative measures, values, relationships or the like (e.g., planar, coplanar, perpendicular). Unless otherwise stated, any one or more if not all of these may be absolute or approximate to account for acceptable variations that may occur, such as those due to engineering tolerances or the like. Like reference numerals refer to like elements throughout.

Example implementations of the present disclosure are directed to simulation of current spectral reflectance across the electromagnetic spectrum provided by hyperspectral data using material information and very limited multispectral samples.

FIG. 1 illustrates a system 100 for implementing a self-calibrating database of spectral data, according to example implementations of the present disclosure. The system is configured to perform a number of different functions or operations, either automatically, under direct operator control, or some combination of thereof. In this regard, in some examples, the system is configured to perform one or more of its functions or operations automatically, that is, without being directly controlled by an operator. Additionally or alternatively, in some examples, the system is configured to perform one or more of its functions or operations under direct operator control.

The system 100 may include one or more of each of any of a number of different subsystems (each an individual system) for performing one or more of its functions or operations. As shown, in some examples, the system includes a calibration subsystem 102 and validation subsystem 104 coupled to one another. Although being shown together as part of the system, it should be understood that either of the subsystems may function or operate as a separate system without regard to the other. And further, it should be understood that the system may include one or more additional or alternative subsystems than those shown in FIG. 1.

According to some example implementations, the calibration subsystem 102 is generally configured to receive remotely-sensed spectral data for a geographic location, and access spectral data for a composition of materials at the geographic location from a database 106 of spectral data for compositions of materials at respective geographic locations. The spectral data for the composition is a mixture of spectral data for the materials in respective percentages in the composition. In some examples, the remotely-sensed spectral data is remotely-sensed multi-spectral data, and the spectral data for the composition is a set of materials and corresponding spectral signatures accessed from a database of material spectral signatures. In these examples, the spectral data for the composition is a mixture of the corresponding spectral signatures for the materials in respective percentages in the composition.

The calibration subsystem 102 is configured to calibrate the spectral data to match the remotely-sensed spectral data and thereby configured to produce calibrated spectral data for the composition in which the materials are in respective percentages at least one of which is different from the spectral data. The validation subsystem 104 is generally configured to validate the calibrated spectral data for the composition; and in an instance in which the calibrated spectral data for the composition is validated, replace the spectral data with the calibrated spectral data in the database 106 of spectral data to produce an enhanced database of spectral data for use in identifying materials or compositions of materials therefrom.

In some examples, the calibration subsystem 102 is configured to repeatedly receive remotely-sensed spectral data, access spectral data from the database 106 of spectral data, and calibrate the spectral data, and the validation subsystem 104 is configured to repeatedly validate the calibrated spectral data, and replace the spectral data with the calibrated spectral data in the database, for different remotely-sensed spectral data to further enhance the enhanced database of spectral data. And in at least one instance, the validation subsystem is configured to output identifiers of the materials in the composition of materials.

In some examples, the calibration subsystem 102 employs machine learning. In these examples, the calibration subsystem is configured to associate the remotely-sensed spectral data with the composition of materials in the respective percentages in a training set of a machine learning algorithm. In some examples, then, the calibration subsystem is further configured to use the machine learning algorithm to identify another composition of materials in respective percentages based on the training set that includes previous calibration results, and produce spectral data for the other composition of materials in the respective percentages. In particular, the spectral data for the other composition is calibrated to match the remotely-sensed spectral data and thereby produce calibrated spectral data for the other composition. The calibrated spectral data for the other composition is validated by the validation subsystem 104, and the spectral data for the composition is replaced with the spectral data for the other composition in the database 106 of spectral data.

Figure 2:
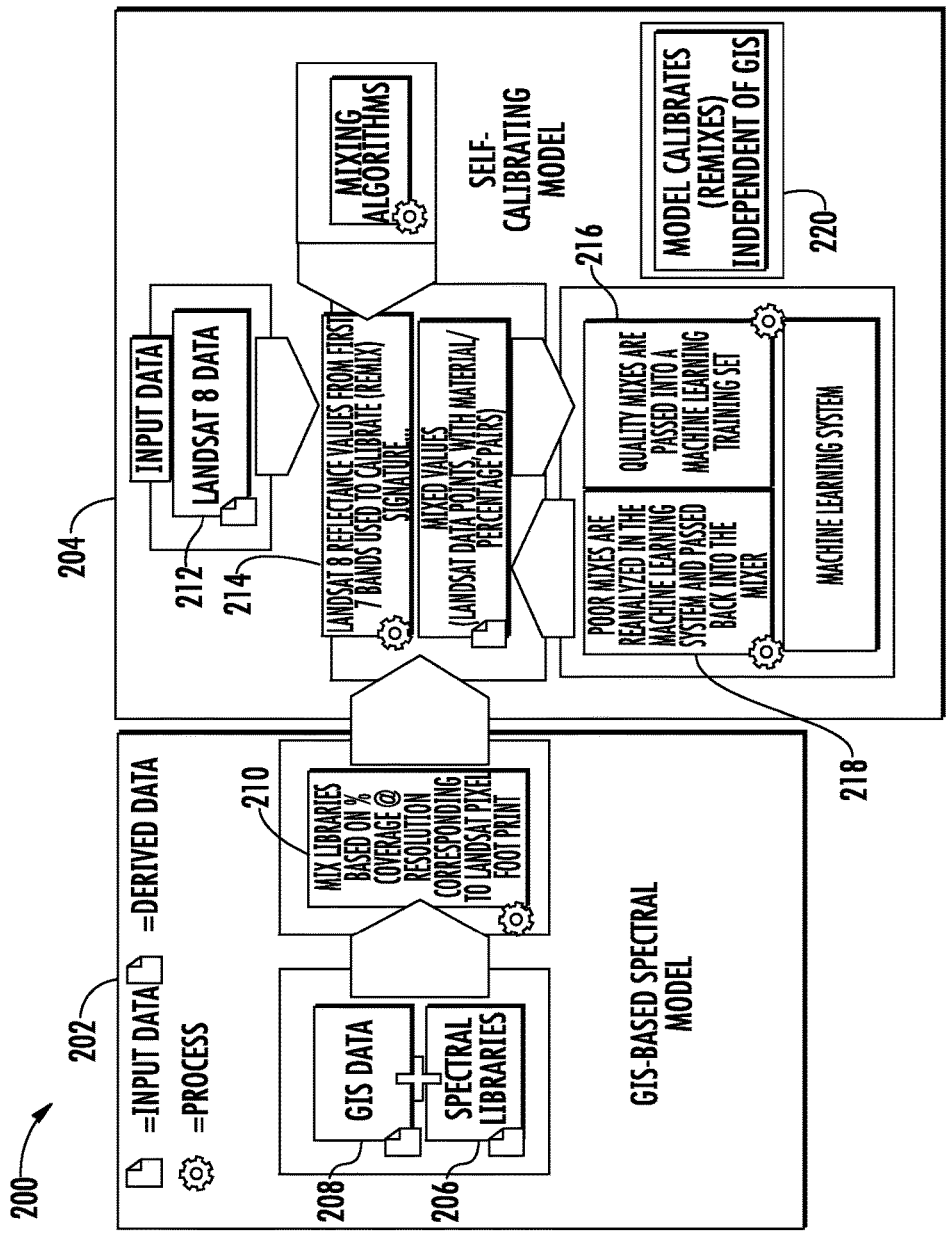
FIG. 2 illustrate illustrates an example implementation of the system of FIG. 1 in the form of a self-calibrating spectral model tool, according to example implementations.

In some examples the calibration subsystem 102 is configured to use the machine learning algorithm to identify the other composition of materials further based on the database 106 of spectral data for compositions of materials at respective geographic locations. And in some examples, the calibration subsystem is configured to access spectral data for the materials in the other composition from a library of spectral data, and configured to mix the spectral data for the materials in the other composition in the respective percentages to produce the spectral data for the other composition. To further illustrate example implementations of the present disclosure, FIG. 2 illustrates an example implementation of the system 100 for implementing a self-calibrating database of spectral data in the form of a self-calibrating spectral model (SCSM) tool 200 that demonstrates systems and methods that model spectral information of grids of points on earth using sampled spectral signatures fused with land information GIS data, such as those described in the above cited and incorporated '136, '137 and '141 applications. The SCSM tool also builds on these systems and methods by calibrating to remotely-sensed spectral data using machine learning. The SCSM tool supports several applications, including sensor configuration analysis and planning, simulation of sensors over large areas, anomaly detection, and signature/feature/material detection capabilities. The capabilities enabled by the SCSM tool are considered simulated spectra, or "simSpec." Technology focus areas that may benefit from the SCSM tool include autonomous systems, remote sensing (satellite, aerial, ISR), and any system that can leverage GIS data.

The SCSM tool 200 is based on several data sources. The SCSM tool is modular and configured to abstract out the data sources and allow for utilization of additional GIS data, spectral libraries, and remote sensing information (remotely-sensed spectral data) to create and calibrate spectral data in the model of spectral information for geographic areas (locations). The SCSM tool may use GIS data from any of a number of different sources. In one example, GIS data may be from the United States Geological Survey (USGS), although most polygon GIS datasets that describe land-based classification information can be used. These data types include soils, land use land cover (LULC), waterway and wetlands, and seasonal precipitation information. For known hierarchies, such as the hierarchies used in the USGS LULC databases, the mappings between spectral libraries and corresponding land cover classifications can be applied across the entire continental United States and OCONUS US holdings.

Like the GIS data, the SCSM tool 200 may use spectral libraries from any of a number of different sources. In some examples, the SCSM tool is influenced by the spectral and spatial resolutions of the imagery data source (e.g., LandSat 8) and includes approximately 3,000 specific spectral libraries. Examples of suitable spectral libraries include those from NASA's Jet Propulsion Lab ASTER Spectral Library, and the National Institute of Standards and Technology (NIST) Material Measurement Laboratory Chemical Web Book. These sources are enough to generate a highly effective model, although additional spectral libraries and higher spectral and spatial resolutions of calibration sources may be used to generate more precise and higher resolution models.

The SCSM tool 200 also utilizes remote sensing information (remotely-sensed spectral data) from one or more of a number of different sources. In one example, the remote sensing information includes Landsat 8 data, which provides cost efficiency and consistent, recent collection. Spectral resolution provides enough data points in the visible and SWIR end of the electromagnetic spectrum to support calibration/recalibration. While there are imagery sources available for the SCSM tool that have higher numbers of bands (spectral resolution), Landsat 8 provides the data requirements for reliable data calibration.

As illustrated in FIG. 2, in some examples, the SCSM tool 200 includes a GIS-based spectral model 202, and a self-calibrating data 204. The GIS-based spectral model in some examples simulates spectral information for geographic areas (locations) and thereby performs geographic information system (GIS)-based spectral simulation, such as in accordance with the systems and methods described in the '136, '137 and '141 applications. More particularly, in some examples, the GIS-based spectral model receives GIS data 206 and spectral libraries 208, and assigns spectral libraries to each feature type in covered geographic areas (deciduous forest, coniferous forest, built up area, grasslands, etc.), such as using a best fit technique. As shown at block 210, the GIS-based spectral model performs an initial mixing of the signatures that are found in the GIS dataset, resulting in a "first cut" at spectral mixing—a calculated signature, the component materials and the percentage of each. This initial mixing is then provided to the self-calibrating data 204, which in some examples may implement the calibration and validation subsystems 102, 104.

As shown a block 212, the self-calibrating data 204 also receives remotely-sensed spectral data, here in the form of the seven frequency bands of Landsat 8 reflectance information that cover the visual, near infrared and short wave infrared, which the self-calibrating data uses to calibrate the signatures of each pixel. In some examples, the larger wavelength bands are not used because they are more susceptible to thermal influences, which vary by time of day. Of the seven bands used, the bands covering shorter wavelengths receive a higher weight than those with shorter wavelengths. As shown at block 214, the self-calibrating data recalibrates each area is recalibrated; and as each area is recalibrated, the resulting seven Landsat data points are fed into a machine learning system training set, as shown at block 216. And the data points are mapped back to the calculated composition materials and percentages.

In instances in which a land cover is incorrectly classified and does not match the Landsat information in all seven bands, the Landsat data points covering the area are tested against the machine learning training set to determine a better starting point for mixing, as shown at block 218. This is the self-calibrating portion of the SCSM tool 200.

In some examples, once there is enough data in the training set, the land cover information of the GIS-based spectral model 202 is disconnected from the SCSM tool 200, leaving the self-calibrating spectral model 204, as shown at block 220.

The self-calibrating spectral model 204 is the foundation for several remote sensing data exploitation capabilities, referred to simSpec capabilities such as sensor configuration analysis and planning, simulation of sensors over large areas, anomaly detection, and signature/feature/material detection capabilities. Implemented for automated sensor configuration and analysis, the self-calibrating spectral data can be implemented to determine how effective a given sensor would be in a specific geographical area before flying a sensor or, identify optimal configurations before building the sensor. Implemented for efficient analysis of spectral information, the self-calibrating spectral model 204 can be implemented to automate the identification of relevant bands for a given (small) area, when compared to one or more materials in question. This makes it possible to determine which wavelengths matter and what analysis should be (automatically) performed, which is specific to the materials and the point on earth.

Implemented for anomaly detection, the self-calibrating spectral model 204 can be implemented to show "normal" across the EM spectrum, including many wavelengths that were never sampled. Knowing "normal" and knowing the signature of a material to be detected, the wavelengths where the difference will be detectable can be determined and the cells with the material can be determined.

Implemented for performing a highly-precise change detection, the self-calibrating spectral model 204 can be implemented to identify how specific material compositions may have changed between image captures. Instead of stating that an area has simply changed or that an area has changed from one broad classification to another, the self-calibrating spectral model would make it possible to detect grades of change (i.e. concrete composition increased by X % while chlorophyll-containing deciduous material decreased by Y %). Land Classification GIS data (ex: LULC) can be created by the self-calibrating spectral model using a flexible hierarchy (instead of classifying based on deciduous forest vs coniferous, classify on % of deciduous canopy, grass, exposed soil, wood, etc.).

Figure 3:
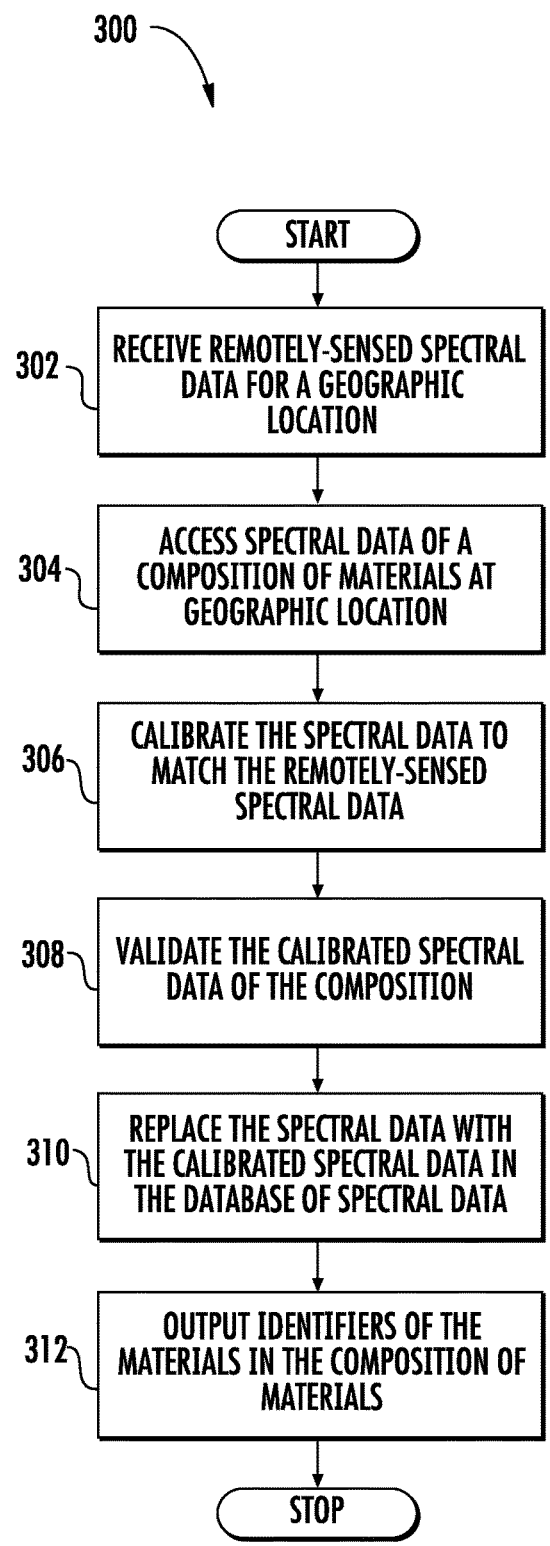
FIG. 3 is a flowchart illustrating various steps in a method according to various example implementations.

FIG. 3 is a flowchart illustrating various steps in a method 300 for implementing a self-calibrating database of spectral data. As shown in block 302, the method includes receiving remotely-sensed spectral data for a geographic location. As shown in block 304 the method includes accessing spectral data for a composition of materials at the geographic location from a database of spectral data for compositions of materials at respective geographic locations, the spectral data for the composition being a mixture of spectral data for the materials in respective percentages in the composition. The method includes calibrating the spectral data to match the remotely-sensed spectral data and thereby produce calibrated spectral data for the composition in which the materials are in respective percentages at least one of which is different from the spectral data, as shown in block 306. The method includes validating the calibrated spectral data for the composition, as shown in block 308. In an instance in which the calibrated spectral data for the composition is validated, the method includes replacing the spectral data with the calibrated spectral data in the database of spectral data to produce an enhanced database of spectral data for use in identifying materials or compositions of materials therefrom, as shown in block 310. And in at least one instance, the method includes outputting identifiers of the materials in the composition of materials, as shown in block 312.

According to example implementations of the present disclosure, the system 100 for implementing a self-calibrating database of spectral data and its subsystems including the calibration subsystem 102 and the validation subsystem 108 may be implemented by various means. Means for implementing the system and its subsystems may include hardware, alone or under direction of one or more computer programs from a computer-readable storage medium. In some examples, one or more apparatuses may be configured to function as or otherwise implement the system and its subsystems shown and described herein. In examples involving more than one apparatus, the respective apparatuses may be connected to or otherwise in communication with one another in a number of different manners, such as directly or indirectly via a wired or wireless network or the like.

Figure 4:
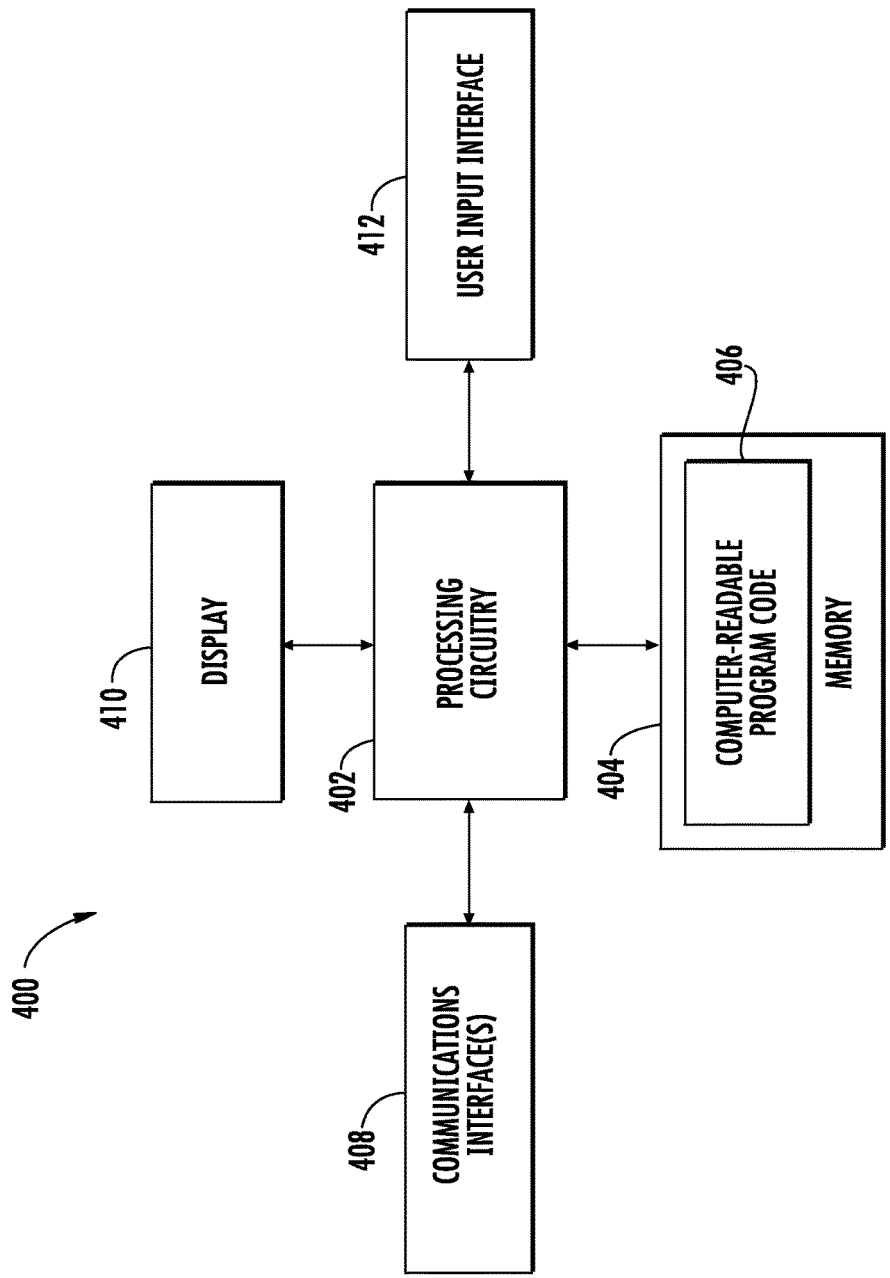
FIG. 4 illustrates an apparatus according to some example implementations.

FIG. 4 illustrates an apparatus 400 according to some example implementations of the present disclosure. Generally, an apparatus of exemplary implementations of the present disclosure may comprise, include or be embodied in one or more fixed or portable electronic devices. Examples of suitable electronic devices include a smartphone, tablet computer, laptop computer, desktop computer, workstation computer, server computer or the like. The apparatus may include one or more of each of a number of components such as, for example, a processor 402 (e.g., processor unit) connected to a memory 404 (e.g., storage device).

The processor 402 may be composed of one or more processors alone or in combination with one or more memories. The processor is generally any piece of computer hardware that is capable of processing information such as, for example, data, computer programs and/or other suitable electronic information. The processor is composed of a collection of electronic circuits some of which may be packaged as an integrated circuit or multiple interconnected integrated circuits (an integrated circuit at times more commonly referred to as a "chip"). The processor may be configured to execute computer programs, which may be stored onboard the processor or otherwise stored in the memory 404 (of the same or another apparatus).

The processor 402 may be a number of processors, a multi-core processor or some other type of processor, depending on the particular implementation. Further, the processor may be implemented using a number of heterogeneous processor systems in which a main processor is present with one or more secondary processors on a single chip. As another illustrative example, the processor may be a symmetric multi-processor system containing multiple processors of the same type. In yet another example, the processor may be embodied as or otherwise include one or more ASICs, FPGAs or the like. Thus, although the processor may be capable of executing a computer program to perform one or more functions, the processor of various examples may be capable of performing one or more functions without the aid of a computer program. In either instance, the processor may be appropriately programmed to perform functions or operations according to example implementations of the present disclosure.

The memory 404 is generally any piece of computer hardware that is capable of storing information such as, for example, data, computer programs (e.g., computer-readable program code 406) and/or other suitable information either on a temporary basis and/or a permanent basis. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD or the like. In various instances, the memory may be referred to as a computer-readable storage medium. The computer-readable storage medium is a non-transitory device capable of storing information, and is distinguishable from computer-readable transmission media such as electronic transitory signals capable of carrying information from one location to another. Computer-readable medium as described herein may generally refer to a computer-readable storage medium or computer-readable transmission medium.

In addition to the memory 404, the processor 402 may also be connected to one or more interfaces for displaying, transmitting and/or receiving information. The interfaces may include a communications interface 408 (e.g., communications unit) and/or one or more user interfaces. The communications interface may be configured to transmit and/or receive information, such as to and/or from other apparatus(es), network(s) or the like. The communications interface may be configured to transmit and/or receive information by physical (wired) and/or wireless communications links. Examples of suitable communication interfaces include a network interface controller (NIC), wireless NIC (WNIC) or the like.

The user interfaces may include a display 410 and/or one or more user input interfaces 412 (e.g., input/output unit). The display may be configured to present or otherwise display information to a user, suitable examples of which include a liquid crystal display (LCD), light-emitting diode display (LED), plasma display panel (PDP) or the like. The user input interfaces may be wired or wireless, and may be configured to receive information from a user into the apparatus, such as for processing, storage and/or display. Suitable examples of user input interfaces include a microphone, image or video capture device, keyboard or keypad, joystick, touch-sensitive surface (separate from or integrated into a touchscreen), biometric sensor or the like. The user interfaces may further include one or more interfaces for communicating with peripherals such as printers, scanners or the like.

As indicated above, program code instructions may be stored in memory, and executed by processor that is thereby programmed, to implement functions of the systems, subsystems, tools and their respective elements described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the computer, processor or other programmable apparatus provide operations for implementing functions described herein.

Execution of instructions by processor, or storage of instructions in a computer-readable storage medium, supports combinations of operations for performing the specified functions. In this manner, an apparatus 400 may include processor 402 and a computer-readable storage medium or memory 404 coupled to the processor, where the processor is configured to execute computer-readable program code 406 stored in the memory. It will also be understood that one or more functions, and combinations of functions, may be implemented by special purpose hardware-based computer systems and/or processor which perform the specified functions, or combinations of special purpose hardware and program code instructions.

Many modifications and other implementations of the disclosure set forth herein will come to mind to one skilled in the art to which the disclosure pertains having the benefit of the teachings presented in the foregoing description and the associated drawings. Therefore, it is to be understood that the disclosure is not to be limited to the specific implementations disclosed and that modifications and other implementations are intended to be included within the scope of the appended claims. Moreover, although the foregoing description and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus for implementing a self-calibrating database of spectral data, the apparatus comprising a processor and a memory storing executable instructions that, in response to execution by the processor, cause the apparatus to:
receive remotely-sensed spectral data for a geographic location;
access spectral data for a composition of materials at the geographic location from a database of spectral data for compositions of materials at respective geographic locations, the spectral data for the composition being a mixture of spectral data for the materials in respective percentages in the composition;
calibrate the spectral data to match the remotely-sensed spectral data and thereby produce calibrated spectral data for the composition in which the materials are in respective percentages at least one of which is different from the spectral data;
validate the calibrated spectral data for the composition; and in an instance in which the calibrated spectral data for the composition is validated,
replace the spectral data with the calibrated spectral data in the database of spectral data to produce an enhanced database of spectral data for use in identifying materials or compositions of materials therefrom; and in at least one instance,
output identifiers of the materials in the composition of materials.

2. The apparatus of claim 1, wherein the remotely-sensed spectral data is remotely-sensed multi-spectral data, and
wherein the spectral data for the composition is a set of materials and corresponding spectral signatures accessed from a database of material spectral signatures, the spectral data for the composition being a mixture of the corresponding spectral signatures for the materials in respective percentages in the composition.

3. The apparatus of claim 1, wherein the apparatus is caused to repeatedly receive remotely-sensed spectral data, access spectral data from the database of spectral data, calibrate the spectral data, validate the calibrated spectral data, and replace the spectral data with the calibrated spectral data, for different remotely-sensed spectral data to further enhance the enhanced database of spectral data.

4. The apparatus of claim 3, wherein the memory stores executable instructions that, in response to execution by the processor, cause the apparatus to further associate the remotely-sensed spectral data with the composition of materials in the respective percentages, the remotely-sensed spectral data being associated with the composition in a training set of a machine learning algorithm.

5. The apparatus of claim 4, wherein the memory stores executable instructions that, in response to execution by the processor, cause the apparatus to further:
use the machine learning algorithm to identify another composition of materials in respective percentages based on the training set that includes previous calibration results; and
produce spectral data for the other composition of materials in the respective percentages,
wherein the spectral data for the other composition is calibrated to match the remotely-sensed spectral data and thereby produce calibrated spectral data for the other composition, the calibrated spectral data for the other composition is validated, and the spectral data for the composition is replaced with the spectral data for the other composition in the database of spectral data.

6. The apparatus of claim 5, wherein the apparatus being caused to use the machine learning algorithm includes being caused to use the machine learning algorithm to identify the other composition of materials further based on the database of spectral data for compositions of materials at respective geographic locations.

7. The apparatus of claim 5, wherein the apparatus being caused to produce the spectral data for the other composition includes the apparatus being caused to:
   access spectral data for the materials in the other composition from a library of spectral data; and
   mix the spectral data for the materials in the other composition in the respective percentages to produce the spectral data for the other composition.

8. A method of implementing a self-calibrating database of spectral data, the method comprising:
   receiving remotely-sensed spectral data for a geographic location;
   accessing spectral data for a composition of materials at the geographic location from a database of spectral data for compositions of materials at respective geographic locations, the spectral data for the composition being a mixture of spectral data for the materials in respective percentages in the composition;
   calibrating the spectral data to match the remotely-sensed spectral data and thereby produce calibrated spectral data for the composition in which the materials are in respective percentages at least one of which is different from the spectral data;
   validating the calibrated spectral data for the composition; and in an instance in which the calibrated spectral data for the composition is validated,
   replacing the spectral data with the calibrated spectral data in the database of spectral data to produce an enhanced database of spectral data for use in identifying materials or compositions of materials therefrom; and in at least one instance,
   outputting identifiers of the materials in the composition of materials.

9. The method of claim 8, wherein the remotely-sensed spectral data is remotely-sensed multi-spectral data, and
   wherein the spectral data for the composition is a set of materials and corresponding spectral signatures accessed from a database of material spectral signatures, the spectral data for the composition being a mixture of the corresponding spectral signatures for the materials in respective percentages in the composition.

10. The method of claim 8, wherein the receiving remotely-sensed spectral data, accessing spectral data from the database of spectral data, calibrating the spectral data, validating the calibrated spectral data, and replacing the spectral data with the calibrated spectral data are repeatedly performed for different remotely-sensed spectral data to further enhance the enhanced database of spectral data.

11. The method of claim 10, wherein in each instance in which the calibrated spectral data for the composition is validated, the method further comprises associating the remotely-sensed spectral data with the composition of materials in the respective percentages, the remotely-sensed spectral data being associated with the composition in a training set of a machine learning algorithm.

12. The method of claim 11, wherein in at least one instance in which the calibrating fails to match the spectral data to the remotely-sensed spectral data, or in which the validating fails to validate the calibrated spectral data, the method further comprises:
   using the machine learning algorithm to identify another composition of materials in respective percentages based on the training set that includes previous calibration results; and
   producing spectral data for the other composition of materials in the respective percentages,
   wherein the spectral data for the other composition is calibrated to match the remotely-sensed spectral data and thereby produce calibrated spectral data for the other composition, the calibrated spectral data for the other composition is validated, and the spectral data for the composition is replaced with the spectral data for the other composition in the database of spectral data.

13. The method of claim 12, wherein using the machine learning algorithm includes using the machine learning algorithm to identify the other composition of materials further based on the database of spectral data for compositions of materials at respective geographic locations.

14. The method of claim 12, wherein producing the spectral data for the other composition includes:
   accessing spectral data for the materials in the other composition from a library of spectral data; and
   mixing the spectral data for the materials in the other composition in the respective percentages to produce the spectral data for the other composition.

15. A computer-readable storage medium that is non-transitory and has computer-readable program code portions stored therein that in response to execution by a processor, cause an apparatus to:
   receive remotely-sensed spectral data for a geographic location;
   access spectral data for a composition of materials at the geographic location from a database of spectral data for compositions of materials at respective geographic locations, the spectral data for the composition being a mixture of spectral data for the materials in respective percentages in the composition;
   calibrate the spectral data to match the remotely-sensed spectral data and thereby produce calibrated spectral data for the composition in which the materials are in respective percentages at least one of which is different from the spectral data;
   validate the calibrated spectral data for the composition; and in an instance in which the calibrated spectral data for the composition is validated,
   replace the spectral data with the calibrated spectral data in the database of spectral data to produce an enhanced database of spectral data for use in identifying materials or compositions of materials therefrom; and in at least one instance,
   output identifiers of the materials in the composition of materials.

16. The computer-readable storage medium of claim 15, wherein the remotely-sensed spectral data is remotely-sensed multi-spectral data, and
   wherein the spectral data for the composition is a set of materials and corresponding spectral signatures accessed from a database of material spectral signatures, the spectral data for the composition being a mixture of the corresponding spectral signatures for the materials in respective percentages in the composition.

17. The computer-readable storage medium of claim 15, wherein the apparatus is caused to repeatedly receive remotely-sensed spectral data, access spectral data from the database of spectral data, calibrating the spectral data, validate the calibrated spectral data, and replace the spectral data with the calibrated spectral data, for different remotely-sensed spectral data to further enhance the enhanced database of spectral data.

18. The computer-readable storage medium of claim 17, wherein the computer-readable storage medium stores executable instructions that, in response to execution by the processor, cause the apparatus to further associate the remotely-sensed spectral data with the composition of materials in the respective percentages, the remotely-sensed spectral data being associated with the composition in a training set of a machine learning algorithm.

19. The computer-readable storage medium of claim 18, wherein the computer-readable storage medium stores executable instructions that, in response to execution by the processor, cause the apparatus to further:

use the machine learning algorithm to identify another composition of materials in respective percentages based on the training set that includes previous calibration results; and produce spectral data for the other composition of materials in the respective percentages, wherein the spectral data for the other composition is calibrated to match the remotely-sensed spectral data and thereby produce calibrated spectral data for the other composition, the calibrated spectral data for the other composition is validated, and the spectral data for the composition is replaced with the spectral data for the other composition in the database of spectral data.

20. The computer-readable storage medium of claim 19, wherein the apparatus being caused to use the machine learning algorithm includes being caused to use the machine learning algorithm to identify the other composition of materials further based on the database of spectral data for compositions of materials at respective geographic locations.

21. The computer-readable storage medium of claim 19, wherein the apparatus being caused to produce the spectral data for the other composition includes the apparatus being caused to:

access spectral data for the materials in the other composition from a library of spectral data; and mix the spectral data for the materials in the other composition in the respective percentages to produce the spectral data for the other composition.

* * * * *